(12) United States Patent
Mervin (10) Patent No.: US 12,364,446 B2
(45) Date of Patent: Jul. 22, 2025

(54) ELECTROMAGNETIC RADIATION POLY-CAPILLARY BLOCK FILTER AND APPLICATIONS THEREOF

(71) Applicant: GOYA DENTAL PTY LTD, West Gosford (AU)

(72) Inventor: Kyle Andrew Mervin, East Gosford (AU)

(73) Assignee: GOYA DENTAL PTY LTD, West Gosford (AU)

( * ) Notice: Subject to any disclaimer, the term of this patent is extended or adjusted under 35 U.S.C. 154(b) by 292 days.

(21) Appl. No.: 18/247,578

(22) PCT Filed: Sep. 15, 2021

(86) PCT No.: PCT/AU2021/051064
§ 371 (c)(1),
(2) Date: Mar. 31, 2023

(87) PCT Pub. No.: WO2022/077050
PCT Pub. Date: Apr. 21, 2022

(65) Prior Publication Data
US 2023/0371908 A1    Nov. 23, 2023

(30) Foreign Application Priority Data
Oct. 13, 2020   (AU) .................... 2020903716

(51) Int. Cl.
*A61B 6/00* (2024.01)
*A61B 6/06* (2006.01)
*A61B 6/40* (2024.01)

(52) U.S. Cl.
CPC .............. *A61B 6/06* (2013.01); *A61B 6/4007* (2013.01)

(58) Field of Classification Search
CPC .. G02B 6/0001; G02B 6/0011; G02B 6/0051; G02B 6/0076; G02B 6/008;
(Continued)

(56) References Cited

U.S. PATENT DOCUMENTS

| | | |
|---|---|---|
| 3,684,886 A | 8/1972 | Muehllegner |
| 4,581,753 A | 4/1986 | Rice |

(Continued)

FOREIGN PATENT DOCUMENTS

| | | |
|---|---|---|
| CN | 1381284 A | 11/2002 |
| CN | 208756805 U | 4/2019 |

(Continued)

OTHER PUBLICATIONS

Written Opinion issued in International Patent Application No. PCT/AU2021/051064, mailing date Nov. 16, 2021.

(Continued)

*Primary Examiner* — Don K Wong
(74) *Attorney, Agent, or Firm* — Benesch Friedlander Coplan & Aronoff LLP (57) ABSTRACT

An electromagnetic radiation collimator comprising: a radiopaque elongated housing having a first end and a second end, wherein the housing houses an array of parallel radiolucent beam paths, wherein each of the beam paths extend from the first end to the second end, wherein each of the beam paths has an entrance aperture at the first end, and an exit aperture at the second end; the entrance aperture through which source electromagnetic radiation passes into the beam paths, wherein the beam paths emits an electromagnetic radiation beam from the exit aperture when the source electromagnetic radiation beams are in line with the longitudinal axis of the beam path or having a predetermined angle of deviation from the longitudinal axis of the beam path.

17 Claims, 7 Drawing Sheets

(58) Field of Classification Search
CPC ....... G02B 6/0095; G02F 1/292; G02F 1/291;
G02F 1/29; G02F 1/295; G21K 2201/061;
G21K 5/02; G21K 5/04; G21K 2201/064;
G21K 5/00; G21K 6/06; G21K 6/08;
A61B 6/06; A61B 6/08
See application file for complete search history.

(56) References Cited

U.S. PATENT DOCUMENTS

| | | | |
|---|---|---|---|
| 6,678,352 | B1 | 1/2004 | Kumakhov |
| 9,966,158 | B2 | 5/2018 | Reitz et al. |
| 2014/0226785 | A1 | 8/2014 | Stutman et al. |
| 2018/0228451 | A1 | 8/2018 | Li et al. |

FOREIGN PATENT DOCUMENTS

| | | | | |
|---|---|---|---|---|
| CN | 111613361 | A | 9/2020 | |
| DE | 102010034597 | A1 | 2/2012 | |
| EP | 3114693 | B1 | 9/2018 | |
| EP | 2904433 | B1 | 1/2020 | |
| JP | 2006337121 | A | 12/2006 | |
| JP | 3871654 | B2 | 1/2007 | |
| JP | 2016085232 | A | 5/2016 | |
| KR | 20190084453 | A | 7/2019 | |
| RU | 2591761 | C2 * | 7/2016 | ............... A61B 6/06 |
| WO | 99/30615 | A1 | 6/1999 | |

OTHER PUBLICATIONS

Extended European Search Report issued in European Patent Application No. 21878775.2, dated Nov. 19, 2024.
Hoffman S. A., et al: "Developments in Tapered Monocapillary and Polycapillary Glass X-Rayconcentrators", Nuclear Instruments & Methods in Physics Research. Section A, Elsevier BV * North-Holland, NL, vol. 347, No. 1/03, Aug. 11, 1994 (Aug. 11, 1994), pp. 384-389, XP000462360,ISSN: 0168-9002, DOI:10.1016/0168-9002(94)91914-3.
Kunio Koyabu et al: "Novel High-Density Collimator Module", Proceedings of the Conference on Optical Fiber Communication / International Conference on Integrated Optics and Optical Fiber Communication (OFC / IOOC). San Jose, Feb. 21-26, 1993; [Proceedings of the Conference on Optical Fiber Communication / I, vol. -, Feb. 21, 1993.
Mineo T et al: "Effects of capillary reflection in the performance of the collimator of the Large Area Detector on board Loft", arxiv.org, Cornell University Library, 201 Olin Library Cornell University Ithaca, NY 14853, Jan. 15, 2014 (Jan. 15, 2014), XP080002035, DOI: 10.1007/S10686-013-9368-8.

* cited by examiner

ELECTROMAGNETIC RADIATION POLY-CAPILLARY BLOCK FILTER AND APPLICATIONS THEREOF

TECHNICAL FIELD

Diagnostic imaging with x-ray radiation based on the notion, that an x-ray originating from a source travels along a straight-line path between the source and the tissue being surveyed, and then on to the sensor. The relative radio opacity of the specimen along that path can be determined by the strength of the beam that reaches the sensor, compared with the strength of the beam that leaves the source. Adjacent and parallel paths can then be used to form a 2 dimensional image.

Conventional designs are hampered by the scatter produced when stray x-rays interact with various materials within their straight-line pathway between the x-ray source and the sensor. Additionally, the x-ray source (focal spot) more approximates a point source producing x-ray photons that propagate in divergent paths and cannot by definition produce beams that are parallel.

The present invention is a device that utilizes the properties of x-ray radiation to produce a series of beams that are approaching parallel, such that the radio-lucency/radio-opacity of specific parallel pathways through the tissue can be accurately determined and simply measured.

The present invention is a filter that can be used to condition the beam emerging from an x-ray (or other EM radiation emitting) tube into a series of distinct beams closely approximating parallel. The device is constructed out of radio-opaque material, which creates a physical barrier to the passage of unwanted/non-parallel beams, whilst selectively allowing beams that are parallel (or nearing parallel relative to each other) to emerge from the diagnostic end of the device. Thus allowing for diagnostic imaging to be based on a parallel beams. The present device is designed to either replace the conventional collimator or retrofit an x-ray unit between the collimator and specimen to further modify the diagnostic beam.

BACKGROUND

A conventional x-ray tube has three elements responsible for the composition of a diagnostic beam. The focal spot, which generates the primary x-rays, a filter which selectively removes useless x-rays, and becomes a secondary source of x-rays, and a collimator which provides a physical, radio-opaque barrier to divergent beams.

Typically, collimation of X-rays enhances the image quality of an X-ray imaging system. Collimation is important for image quality as collimation of an X-ray source reduces the amount of scattered X-ray photons which reach the X-ray sensor elements, after having passed through the subject matter being imaged. These scattered X-ray photons would otherwise contribute to the reading from the sensor elements and reduce the overall contrast in the X-ray image because they do not convey the same relevant diagnostic information as the unscattered or parallel X-ray photons that have passed directly from the X-ray source to the sensor element. Scattered photons are responsible for the haziness often associated with radiographs.

Conventional X-ray collimators uses an anti-scatter grid, which can be a two-dimensional grid, positioned directly in front of the sensor and the grid serves to absorb or block photons emanating with a large angle. These grids are often grid structures composed of high-density metals. A possible limitation of such grid structures is that the photons emanating with lower angles may still be considered a large angle of deviation from the longitudinal axis of the path of the beam, thereby still considered as allowing scattered photons.

An example of such a two-dimensional X-ray source is provided in WO2011/017645 apparatus for producing X-rays for use in imaging. Known collimation and lensing methods are not so useful for collimating a two-dimensional array of X-ray sources and it is an aim of the embodiments of the present invention to at least partially mitigate the disadvantages of known X-ray collimation methods and to provide a means of collimating X-rays whereby multiple collimating elements or holes allow for the passage of x-ray photons derived from a scatter medium distinct from the primary x-ray source (focal spot).

For example, Australian Patent No. 2015225939 describes an X-ray collimator and a method of obtaining an X-ray image and finds utility in the collimation of X-ray Bremsstrahlung radiation, where the X-ray source comprises a plurality of X-ray sources arranged in a two-dimensional array. Another example, U.S. Pat. No. 8,774,351 describes an apparatus and method for X-ray imaging a human patient. However, these examples may use collimators that have relatively large beam path sizes that may not significantly filter out non-diagnostically valuable photons for medical imaging, thereby may produce a relatively hazy or a relatively low-resolution image of the subject region of interest. While examples of collimating X-ray radiation have been discussed in detail, this principle is also applicable to collimation of other medically useful electromagnetic radiation. That is, even if it is another type of electromagnetic radiation, by not significantly filtering out non-diagnostically valuable photons, it may also produce the similar result of producing low-resolution image of the subject region of interest.

In light of the aforementioned disadvantages, there exists a long-felt need to provide an improved electromagnetic radiation collimator for ultimately producing high resolution medical images when diagnostically valuable photons are selectively passed through when the beams are either in line with the longitudinal axis of the beam path or a relatively minute angle of deviation from the longitudinal axis of the beam path.

Any discussion of the prior art throughout the specification should in no way be considered as an admission that such prior art is widely known or forms part of common general knowledge in the field.

SUMMARY

Problems to be Solved

It may be advantageous to provide an electromagnetic collimation device, that facilitates accurate 2-dimensional measurements of target tissues.

It may be advantageous to provide an electromagnetic radiation collimator that can be retrofitted to existing X-ray machines or other electromagnetic radiation generating machines.

It may be an advantage to provide an array of beam paths in the elongate housing, in which each of the beam paths has a width suitable for use for a particular type of electromagnetic radiation.

It may be an advantage to provide an elongate radio-opaque housing that can house an array of radiolucent tubes.

It may be an advantage to provide a central tube for engaging with a spinning motor to allow the elongate housing to spin.

It may be an advantage to provide an array of beam paths, each having a sufficient length so that the propagated electromagnetic radiation through the beam path will emit a beam in a narrow angle cone.

It may be an advantage to provide a second collimator similar to the first collimator between the subject region of interest and the detector.

It is an object of the present invention to overcome or ameliorate at least one of the disadvantages of the prior art, or to provide a useful alternative.

Means for Solving the Problem

A first aspect of the present invention may relate to an electromagnetic radiation collimator comprising: a radiopaque elongated housing having a first end and a second end, wherein the housing houses an array of parallel radiolucent beam paths, wherein each of the beam paths extend from the first end to the second end, wherein each of the beam paths has an entrance aperture at the first end, and an exit aperture at the second end. The entrance aperture through which source electromagnetic radiation passes into the beam paths, wherein the beam paths emits an electromagnetic radiation beam from the exit aperture when the source electromagnetic radiation beams are in line with the longitudinal axis of the beam path or having a predetermined angle of deviation from the longitudinal axis of the beam path.

Preferably, the array of parallel radiolucent beam paths is an array of parallel radiolucent tubes, wherein each of the tubes defines a lumen for providing the beam path, and wherein the radiolucent tubes are embedded in the elongate housing.

Preferably, the elongate housing is composed of a linear series of alternating first and second layers offset relative to each other, wherein the first layer comprises a first set of apertures each having a first shape, and the second layer comprises a second set of apertures each having a second shape, wherein the first shape and the second shape are partially intersecting such that the series of intersected shapes defines a lumen for providing the beam path. Preferably, the elongate housing is composed of a single block with patent lumen running parallel to the long axis of the block, with the spatial separation of the individual lumen defining the resolution of the diagnostic image.

Alternatively, the elongate housing may be composed of segments arranged in series, with the lumen embedded in each segment offset, so that the beam that emerges from the device is further refined.

Preferably, the first elongated housing has a length longer than the second elongated housing, the width of the entrance aperture of the first elongated housing is smaller than the width of the entrance aperture of the second elongated housing.

Preferably, the predetermined angle of deviation from the longitudinal axis of the beam path is less than 10°. More preferably, the predetermined angle of deviation from the longitudinal axis of the tubes is less than 1°. Desirably, the predetermined angle of deviation from the longitudinal axis of the tubes is 0°.

Preferably, the material of the elongate housing is one selected from the group of: aluminium, zirconia, titanium or lead or any particulate matter that is radio-opaque and can be bound in a resin for 3-dimensional printing or production purposes.

Preferably, the elongate housing comprises at least a groove, wherein the grooves is adapted to engage to a spinning motor for spinning or oscillating the elongate housing.

Preferably, each of the grooves is 3 mm deep, and a width of 5 mm wide.

Preferably, the width of each beam paths is 100 microns.

Preferably, the electromagnetic radiation is one selected from the group of: X-ray radiation, and UV-C radiation.

Preferably, the width of the entrance and exit apertures for use with X-ray radiation are relatively smaller than width of the entrance and exit apertures for use with microwave radiation.

In a second aspect of the present invention may relate to an electromagnetic radiation imaging device adapted for use with two electromagnetic radiation collimators according to the first aspect, wherein the device comprises: an electromagnetic radiation source for generating electromagnetic radiation. The electromagnetic radiation collimator positioned between the radiation source and the subject region, such that the subject region is subjected to parallel electromagnetic radiation from the collimator. The second electromagnetic radiation collimator positioned between the subject region and an electromagnetic radiation detector, wherein the second electromagnetic radiation collimator is adapted for filtering out scattered radiation after propagating through the subject region such that the radiation that reaches the diagnostic sensor is a more accurate indication of the radio-lucent properties of the subject within the path of the diagnostic beam.

Preferably, for X-ray radiation, the primary electromagnetic radiation source is a rotating anode X-ray source offset from the longitudinal axis of the device, such that there are no direct x-ray photons between the source and the sensor.

Preferably, for UV-C radiation, the primary electromagnetic radiation source is a UV lamp.

Preferably, the electromagnetic radiation detector is an X-ray film or x-ray sensor for X-ray radiation, or a UV-C light sensor.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

DESCRIPTION OF THE INVENTION

Preferred embodiments of the invention will now be described with reference to the accompanying drawings and non-limiting examples. It should be noted in the following description that like or the same reference numerals in different embodiments denote the same or similar features.

Figure 1:
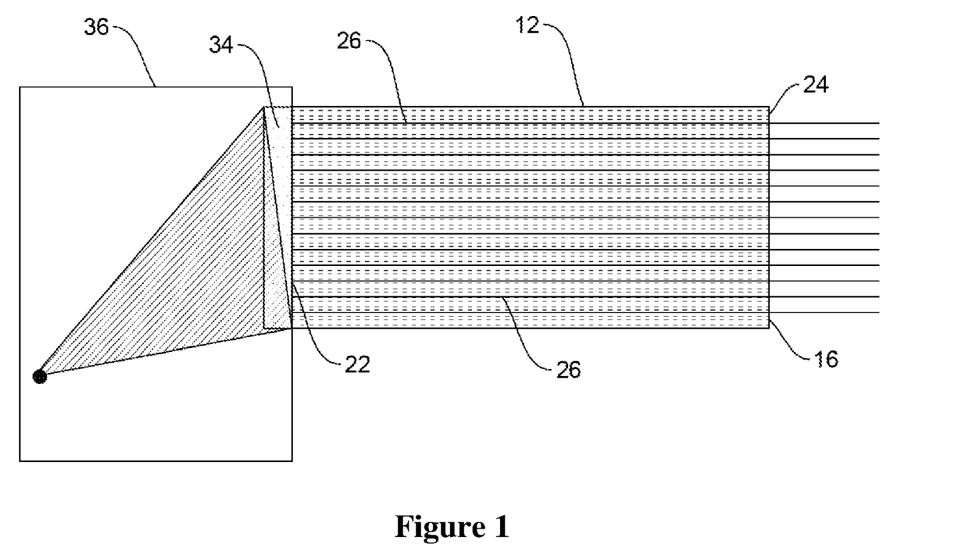
FIG. 1 illustrates the device mounted to and in use with an electromagnetic radiation generation apparatus such that electromagnetic radiation that enters the device in line with the beam paths of the device are emitted from the exit end of the device in parallel lines.
Figure 2:
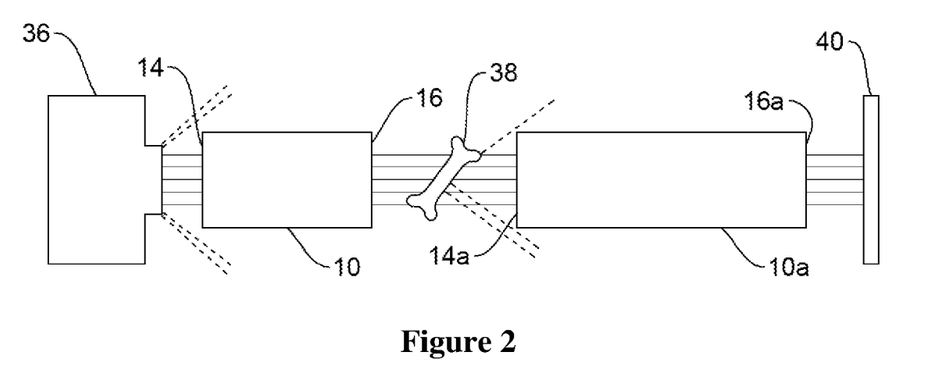
FIG. 2 illustrates a schematic of a first device positioned between the electromagnetic radiation generation apparatus and the subject, and a second similar device positioned between the subject and the detector. The first and second device allows electromagnetic radiation that are in line with the beam paths of the devices to traverse through and filters away the scattered beams such that only parallel radiation reaches the detector.
Figure 3:
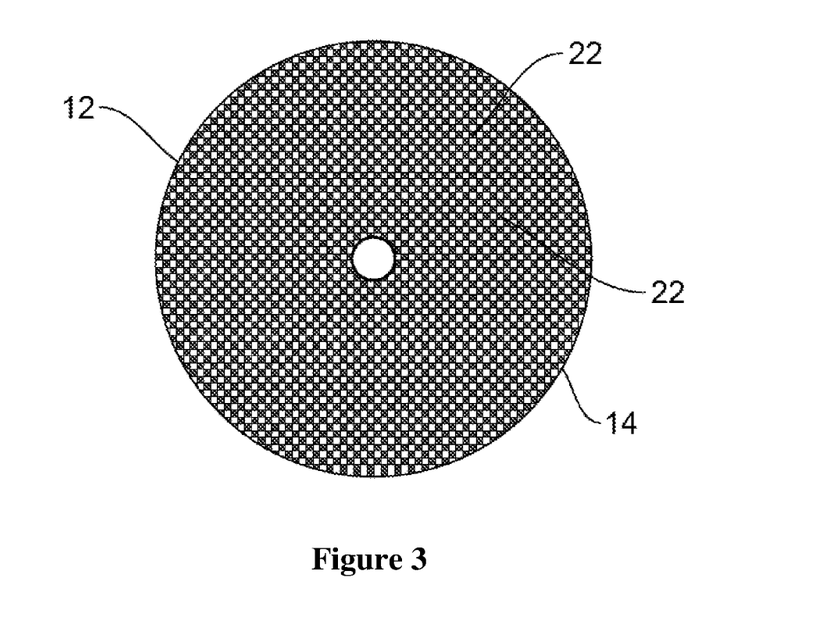
FIG. 3 illustrates a vertical cross-sectional view of the device showing the array of entrance apertures at the first end. It may be appreciated that it may also be a vertical cross-sectional view of the device showing the array of exit apertures at the second end.
Figure 4:
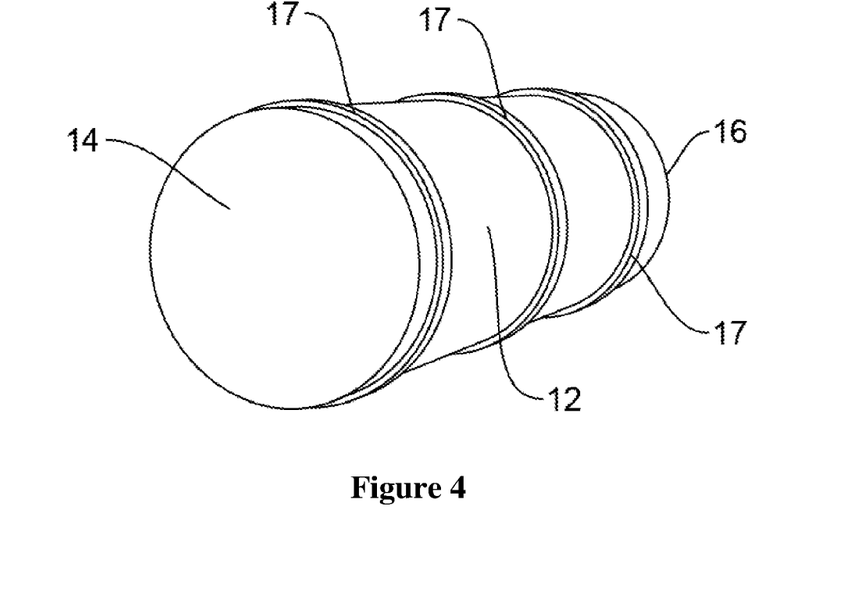
FIG. 4 illustrates a perspective view of the device showing the grooves that are adapted to connect to a motor which allows the device to be rotated, when in use.

In an embodiment of the present invention, as illustrated in FIGS. 1 and 2, the filter/collimator 10 or device 10 (FIG. 2) may be a member 12 (FIG. 1), in which the shape of the member may be an elongated rectangular housing shape or a cylindrical shape. The member may be radiopaque. The rectangular housing member 12 may have a first end 14 and a second end 16. The first end 14 may also be the entrance side 14 of the member 12, and the second end 16 may also be the exit side 16 of the member 12. As shown in FIG. 3, the first end 14 may have a central hole 15, which may be adapted to receive a rod 20 engaging a spinning motor for spinning the member 12. An external lateral view of the member 12 where the external grooves 17 used for securing the device in position, or in the alternate used to mount the device for the purpose of spinning is shown in FIG. 4. As shown in FIG. 4, preferably, each of the grooves is 3 mm deep, and a width of 5 mm wide.

As illustrated in FIG. 3, the first end 14 may have an array of entrance apertures 22. The array of entrance apertures 22 may be in a regular pattern such that the entrance aperture and the adjacent entrance aperture 22 are equidistant relative to each other. As the member may be a rectangular housing or a cylindrical shape, FIG. 3 may also depict a second end 16 having an array of exit apertures 24. The array of exit apertures 24 may also correspond to the same regular pattern as the first end, such that the exit aperture and the adjacent exit aperture 24 are similarly equidistant relative to each other. Between the entrance aperture 22 at the first end 14 and the corresponding exit aperture 22 at the second end 16 is a radiolucent beam path 26. The beam path 26 may be a straight path such that electromagnetic radiation, such as X-ray beams, visible light beams or UV light beams, which are in line with the longitudinal axis of the beam path can enter the entrance apertures 22, and are allowed to pass through the entirety of the beam path of the member 12, and then emit the beam at the corresponding exit aperture 24.

Figure 5:
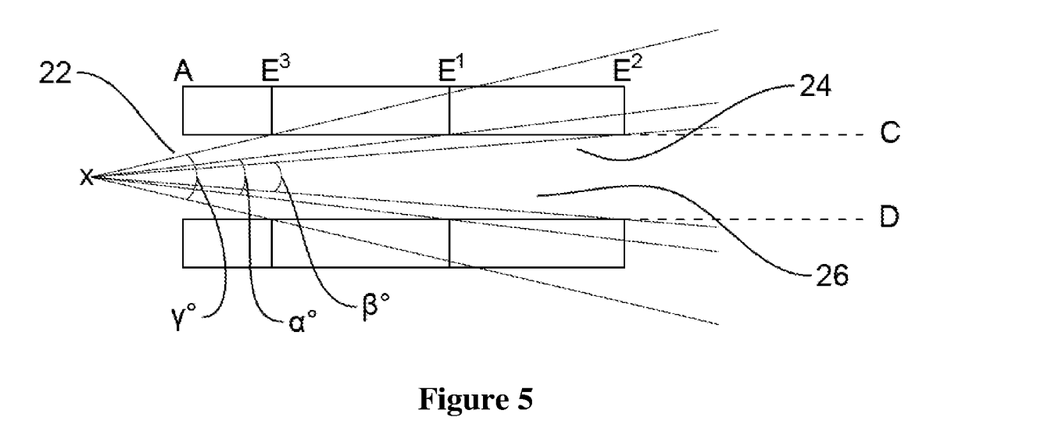
FIG. 5 illustrates a beam path of width $C^1$-$D^1$ with length A-E. Between the beam path and an adjacent beam path, the material of the device may have a thickness of $C^1$-$C^2$ or $D^1$-$D^2$.
Figure 6:
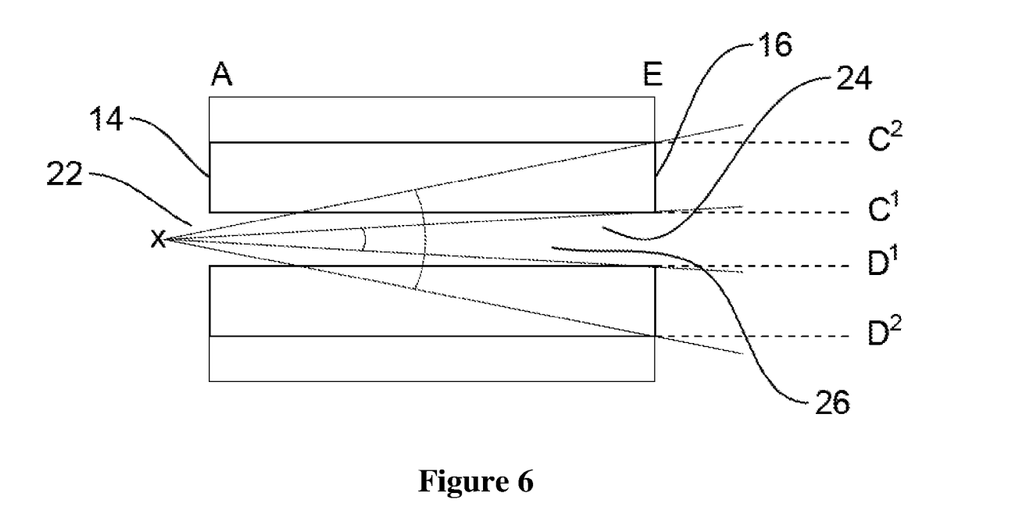
FIG. 6 illustrates a beam path of width C-D with variable lengths A-$E^3$, or A-$E^1$, or A-$E^2$ showing the allowable angle of deviation from the longitudinal axis of the beam paths from the electromagnetic radiation source.

As shown in FIGS. 5 and 6, while the source electromagnetic radiation which are in line with the longitudinal axis of the beam path 26 are preferred, it may be appreciated that a small predetermined angle of deviation from the longitudinal axis of the beam paths can also enter the entrance aperture 22 and also allowed to traverse through the entirety of the beam path of the member 12 and then emit the X-ray beam at the exit aperture 24. Comparing the width of the beam paths 28 of FIGS. 5 and 6, the width of beam path 26 $C^1$-$D^1$ of FIG. 5 has a smaller width than the beam path of FIG. 6 C-D. As such, the predetermined angles allowable for source electromagnetic radiation to traverse the length of the beam path 30 A to E, is relatively smaller than the predetermined angles allowed for a larger width of the beam path 26 A-$E^2$. Preferably, the width of each beam paths is 100 microns.

Further, comparing the length of the beam paths A-$E^3$ and A-$E^1$ and A-$E^2$; the length of the beam path for A-$E^2$ is longer than length of the beam path for A-$E^1$, and the length of the beam path for A-$E^1$ is longer than the length of the beam path for A-$E^3$. When the source radiation focal point X is of a consistent distance from the member 12, the allowable angles of deviation for length A-$E^2$ less than $\beta°$ with respect to the central longitudinal axis of the beam path. Similarly, the allowable angles of deviation for length A-$E^1$ is less than $\alpha°$ with respect to the central longitudinal axis of the beam path, and similarly, the allowable angles of deviation for length A-$E^3$ is less than $\gamma°$ with respect to the central longitudinal axis of the beam path. As shown in FIG. 6, when the beam paths 26 are longer, the allowable range for the angle is smaller, which is more desirable as the emitted radiation from the exit aperture will be as close to being in line with the longitudinal axis of the beam paths as possible. When the source electromagnetic radiation beams are entering the entrance aperture 22 at an angle that is greater than the predetermined angles of deviation, the electromagnetic radiation beam will enter partially into the beam path 26 before striking the radiolucent material that defines the beam path 26. As such, that source beam will not be able to emit from the exit aperture 24. The advantage of allowing those parallel electromagnetic radiation beams through is that it improves the resolution of the imaged subject as those parallel electromagnetic radiation beams strike the detector.

It may be appreciated that the device may be constructed from aluminium, zirconia, titanium or lead with beam paths 26 from the array of entrance apertures 22 to the array of exit apertures 24. The device may also be constructed from any particulate matter that is radio-opaque and can be bound in a resin for 3-dimensional printing or production purposes. Preferably, for strengthening the structural support of the member 12, the array of radiolucent beam paths 26 may be an array of radiolucent tubes, in which each of the tubes may define a lumen 26 for providing the beam path 26 and wherein the radiolucent tubes are embedded in the elongate housing. It may be appreciated that instead of cylindrical tubes, rectangular tubes may be used, in which case the array of entrance apertures 22 and the corresponding exit apertures 24 may be have a square aperture profile instead of a circular aperture profile. It may be appreciated that more entrance apertures 22 in the array may allow more source electromagnetic radiation that are in line with the longitudinal axis of beam paths to be used for imaging the subject.

For the elongate member 12, preferably, the beam paths 26 may have a width and length that allows for a small predetermined angle of deviation from each of the longitudinal axis of the beam paths 26. The range of the predetermined angle may be less than 10°. Desirably, the range of the predetermined angle may be less than 2°. Most desirably, the predetermined angle of deviation from the longitudinal axis of the beam paths or radiolucent tubes is 0° or in line with the longitudinal axis of the beam paths 26. The device is constructed from materials such as aluminium or lead with a certain thickness so that X-rays beams cannot penetrate out of the device 10 that are beyond from the acceptable angle of deviation ranges with respect to the beam path. It may be advantageous to provide a tapered shape to the entrance aperture 22 for allowing the spherical X-ray radiation generated from the X-ray tube to enter the array of entrance apertures 22. Preferably, the tapered entrance aperture is parabolic in shape.

Figure 9:
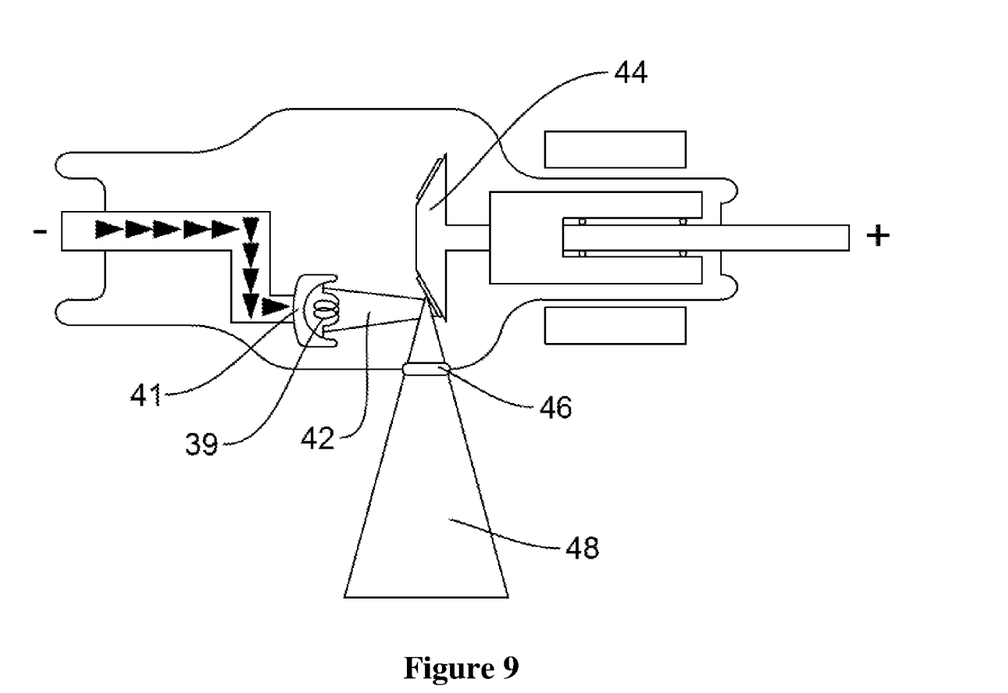
FIG. 9 illustrates a conventional schematic of an X-ray tube showing the parts and the X-ray photon beam emitted from the window of the X-ray tube.

As shown in FIGS. 2 and 9, if using X-rays as the electromagnetic radiation for imaging a subject, there may be an X-ray tube 36 which is a vacuum tube that converts electrical input power into X-rays. As with any vacuum tube, there is a filament or a cathode 39, and a focusing cup 41 which focuses emitted electrons 42 into the vacuum towards the anode or a spinning anode 44 to collect the electrons. This thus establishes a flow of electrical current, which is known as the X-ray photon beam 48, through the window 46 of the X-ray tube 36. A high voltage power source may be used, for example 30 to 150 kilovolts (kV), or the tube voltage, may be connected across the cathode 39 and anode 44 to accelerate the electrons. The X-ray spectrum may depend on the anode material and the accelerating voltage. Electrons from the cathode may collide with the anode material, which may be chosen from tungsten or molybdenum or copper. The electrons from the cathode may accelerate other electrons, ions and nuclei within the anode material. The energy generated may be emitted or radiated, usually perpendicular to the path of the electron beam, as X-rays. The range of photonic energies emitted by this X-ray tube can be adjusted by changing the applied voltage, and installing aluminium filters of varying thicknesses. Aluminium filters may be installed in the path of the X-ray beam to remove soft or non-penetrating radiation. The number of emitted X-ray photons, or dose, are adjusted by controlling the current flow and exposure time. Other tubes such as a rotating anode tube may be used to generate X-rays. For this type, a considerable amount of heat may be generated in the focal spot of a stationary anode, in which the focal spot may be the area where the beam of electrons coming from the cathode strike to. Rather, a rotating anode lets the electron beam sweep a larger area of the anode, thus redeeming the advantage of a higher intensity of emitted radiation, along with reduced damage to the anode compared to its stationary state. Typical anodes are a tungsten-rhenium target on a molybdenum core, backed with graphite. The rhenium makes the tungsten more ductile and resistant to wear from the impact of the electron beams. The molybdenum conducts heat from the target and the graphite provides thermal storage for the anode, and minimises the rotating mass of the anode.

Figure 8:
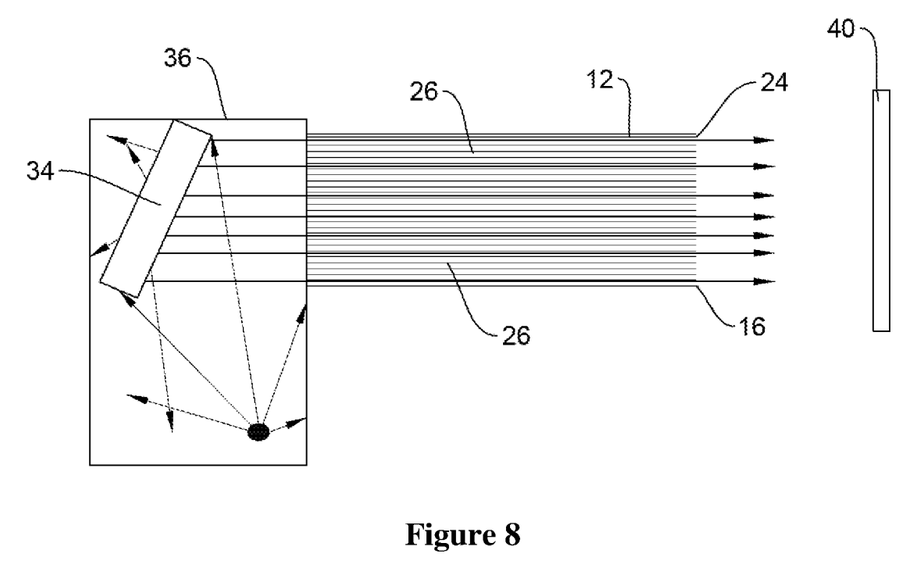
FIG. 8 illustrates the device mounted to and in use with another embodiment of an electromagnetic radiation generation apparatus such that electromagnetic radiation that enters the device in line with the beam paths of the device are emitted from the exit end of the device in parallel lines.
Figure 10:
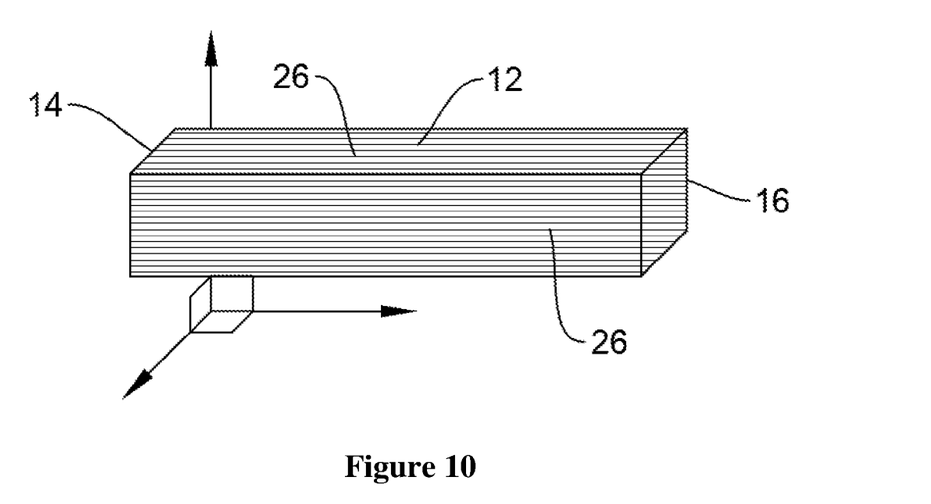
FIG. 10 illustrates a schematic of a parallel imaging field with the x, y, and z axis.
Figure 11:
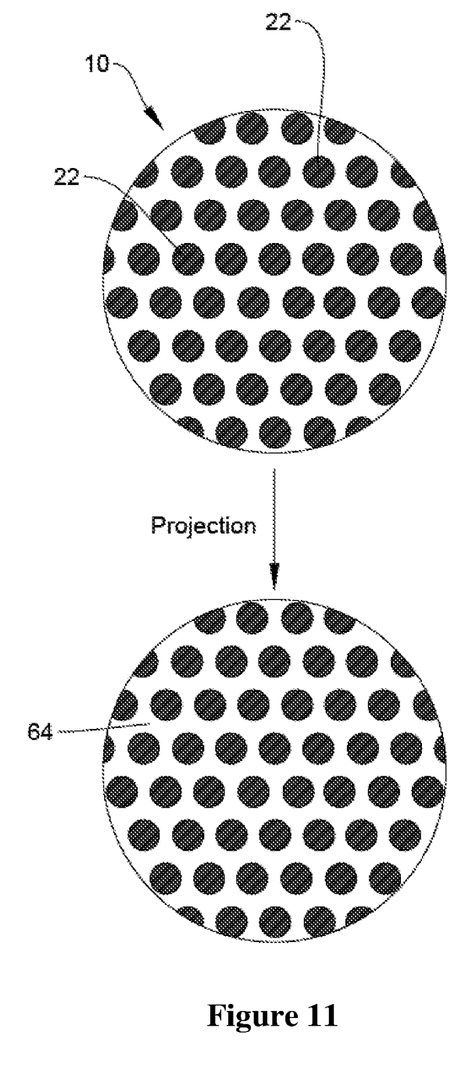
FIG. 11A illustrates the array of apertures in black circles in which the device or filter is static.
FIG. 11B illustrates the projection of the array of apertures of FIG. 11A when static.

As shown in FIG. 1 or 8, there may be an X-ray focal spot within the X-ray tube 36 that may produce X-rays in a spherical manner. The X-ray focal spot may be a primary source of X-rays for this system. A cone of primary X-rays may emanate from the X-ray focal spot which may strike the scatter medium 34, which is positioned between the X-ray generator 32 and the base end 14 of the member 12. The scatter medium 34 may reduce the scattered primary X-ray beams from the source, which then becomes a secondary source of X-rays with a far greater surface area, which then emit X-rays in a random spherical manner. The X-rays then strike the collimator 10, in which any of the X-ray beams that cannot travel entirely through the beam path are filtered away. As such, this collimator 10 selectively allows for parallel X-ray beams that are emitted out the exit apertures 24 of the member 12 in parallel relative to each other in the x axis, which is shown in FIG. 10. The device 10 may be used to direct the parallel X-ray beams to the subject 38 which may be subject to X-ray imaging. FIG. 2 simplistically depicts the skeletal subject 38 as a bone and it is appreciated that for living subjects 38, there are soft tissue surrounding the bone. X-rays do not pass through bones or teeth as calcium from bones or teeth absorb X-rays efficiently so when the skeletal object is placed in the parallel X-ray beam's path, this reduces the amount of X-rays reaching the detector 40 in the shadow of the bones, making them visible on the radiograph. Preferably, hard X-rays are used for X-ray radiography as the low energy or soft X-rays are unwanted since they are totally absorbed by the body, thereby increasing the radiation dose without contributing to the image.

Figure 12:
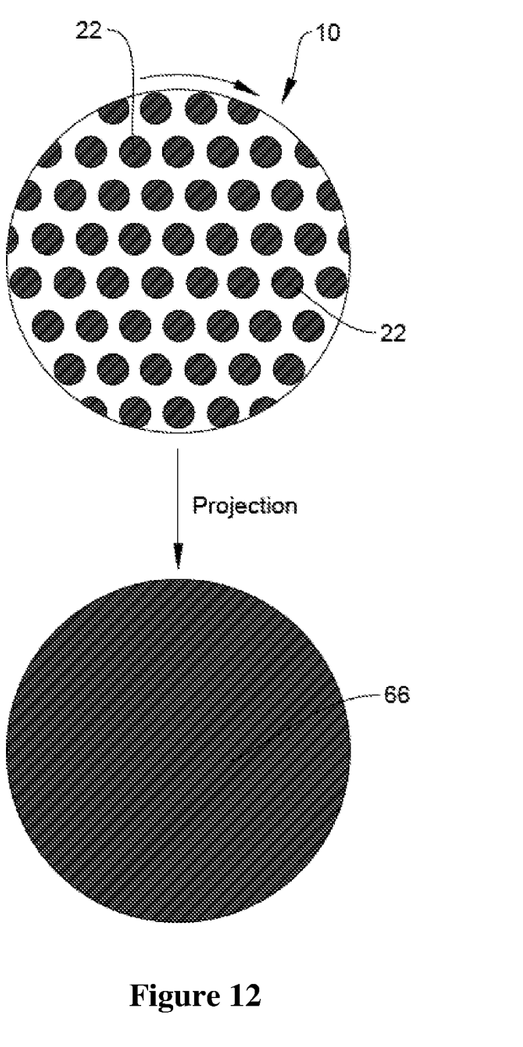
FIG. 12A illustrates the same array of apertures in black circles of FIG. 11A.
FIG. 12B illustrates the projection of the array of apertures of FIG. 12A when rotating.
Figure 13:
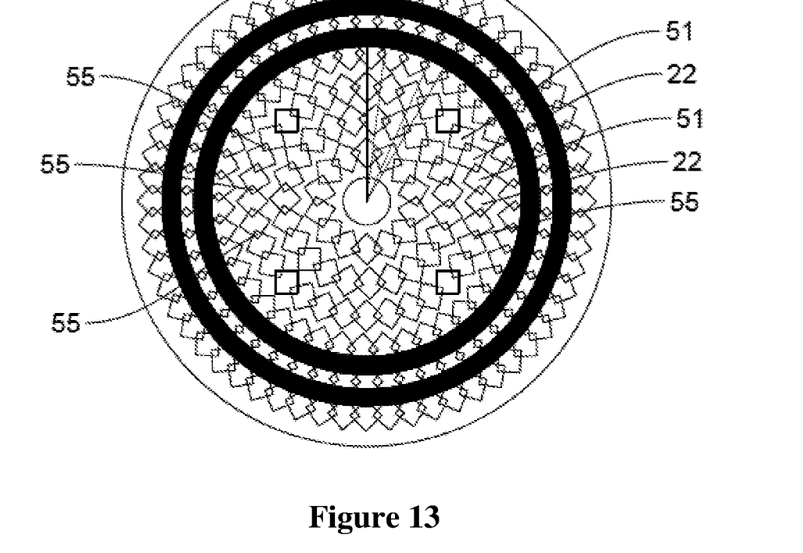
FIG. 13 illustrates a superimposition of lumens from blocks or segments that are equidistant from the central axis producing a projection of concentric circles.

While the device 10 can be used statically, it is preferred that the device 10 is rotated when in use so that the projection have a better coverage. The superior projection coverage is comparatively illustrated between FIG. 11 and FIG. 12. The projection from a static device or filter 10 may have the same projection as the apertures of the filter 64, while the projection from a rotated device or filter 10 may have full projection of a disk 66. While the profile shape of each aperture may be a circle, it may be appreciated that the profile shape of each aperture may be in other shapes. For example, as shown in FIG. 13, the profile shape of each aperture may be a diamond shape.

As living objects have soft tissue surrounding the skeletal object 38, there may be Compton scattering of the parallel X-ray beams that may have deviated from the original parallel path that were emitted from the first collimator 10a when the beams have struck the soft tissue of the object 38. Compton scattering is the predominant interaction between X-rays and soft tissue in medical imaging. Compton scattering is an inelastic scattering of the X-ray photon by an outer shell electron. Part of the energy of the photon is transferred to the scattering electron, thereby ionising the atom and increasing the wavelength of the X-ray. The scattered photon can go in any direction, but a direction similar to the original direction is more likely, especially for high-energy X-rays. As such, a second similar collimator 10a to the first collimator 10 may be used so that the scattered beams are filtered away while the X-ray beams that are parallel to the original X-rays will enter the entrance apertures 22a of the second collimator 10a, which then traverses the entirety of the beam path 26a and then out of the corresponding exit aperture 24a of the second collimator 10a. Once the X-ray beams are emitted from the exit aperture 24a of the second collimator 10a, the parallel X-ray beams then strike the X-ray detector 40 or radiograph. It may be appreciated that as more apertures are in the array, more parallel X-ray beams can be used for imaging which may minimise the haziness of the X-ray image and thereby produce a sharper, clearer and higher resolution X-ray image of the object 38. As haziness or smudgy images may coincidentally cover small abnormalities that may be present; therefore, sharper, clearer and higher resolution X-ray images are most desirable for radiographers, and radiologists to analyse and interpret X-ray images for skeletal objects and other anatomy as well as for dental radiographers to analyse and interpret X-ray images for teeth, which is commonly used in the diagnoses of common oral problems, such as cavities.

Figure 7:
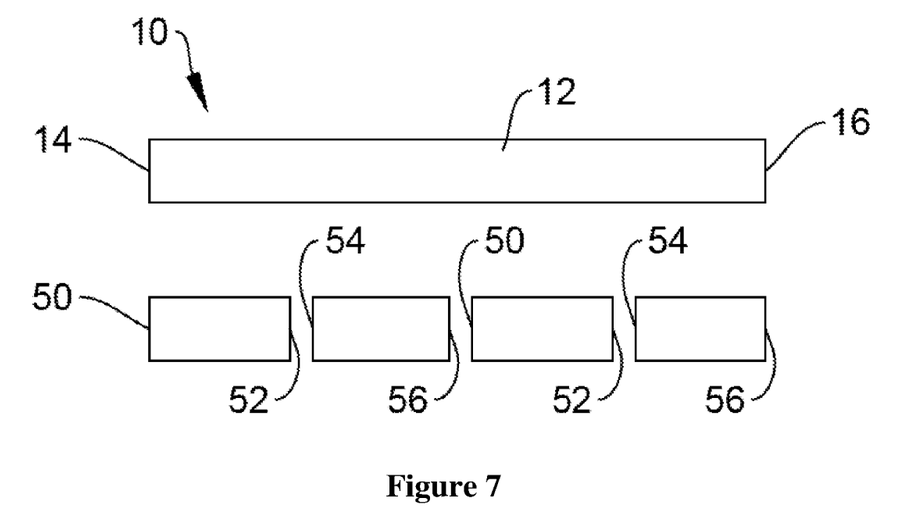
FIG. 7 illustrates a side view of the elongate housing as an integral piece (top) or composed of block or segments (bottom) joined together to similarly form an integral piece.

While the device or collimator 10 may be formed by metal extrusion, it may be appreciated that the device or collimator 10 may be manufactured by materials such as an aluminium alloy which may be suitable for 3D-printing. For example, the aluminium alloy used may be AlSi7Mg0.6. Advantages of manufacturing the device 10 via 3D printing may be rapid prototyping as well as cost-effective in the process of manufacturing. As shown in FIG. 7, the 3D-printed device 10 may be joined by a series of layers or blocks/segments in a linear configuration. The first block/segment may have a first end 50 and a second end 52 and the second block/segment may have a first end 54 and a second end 56. The second end 52 of first block/segment may be joined to the first end 54 of the second block/segment and the second end 56 of the second block/segment may be joined to the first end of a third block/segment, in which the third block/segment may be the same as the first block/segment. Similarly, the fourth block/segment may be the same as the second block/segment. The block/segment may also be termed as a layer.

The first end 50 of the first block/segment or an odd number block/segment in the series may have an array of diamond shaped entrance apertures 22, and the first end 54 of the second block/segment or an even number block/segment in the series may have an array of diamond shaped entrance apertures 51. Similarly, the second end 52 of the first block/segment or an odd number block/segment in the series may have an array of diamond shaped exit apertures 24, and the second end 56 of the second block/segment or an even number block/segment in the series may have an array of diamond shaped exit apertures 59.

Figure 14:
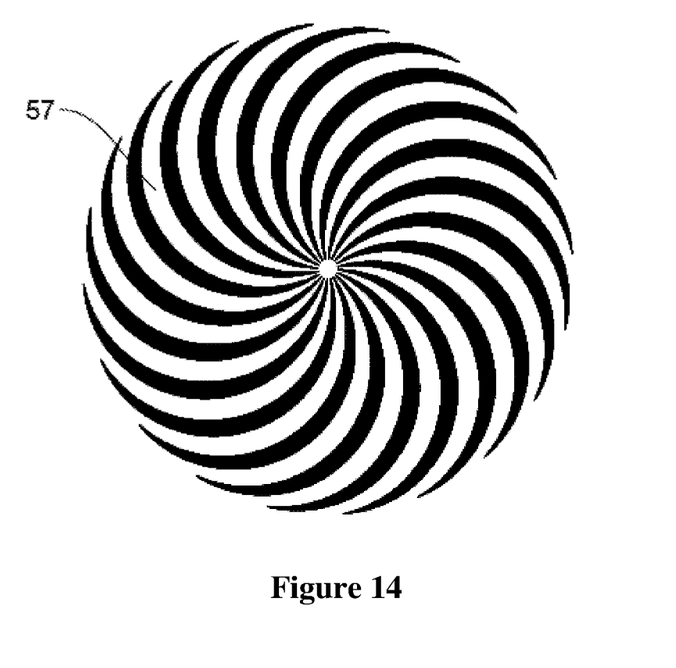
FIG. 14 illustrates the projection of the rotation of the device with the superimposition of lumens are staggered radially from the central axis.

As shown in FIG. 13, the first layer may have a first array of apertures 22 that may have a diamond profile shape. The second layer may have a second array of apertures 51 that may have the same diamond profile shape as the first layer however, the second layer or the subsequent layer may be offset from the first layer such that a right corner of the diamond aperture of the first layer is overlapping or intersecting with a left corner of the second layer thereby forming a smaller diamond shaped aperture 55 for the beam path 26. The third layer with similar apertures as the first layer may be relatively behind the first layer and may be offset to the second layer. Similarly, the fourth layer with similar apertures as the second layer may be relatively behind the second layer and may be offset to the third or previous layer. It may be appreciated that there may be any number of even numbered layers or odd numbered layers to stacked to form the elongate housing as long as the even numbered layers may be relatively offset to the odd numbered layers. This method of manufacture may provide the advantage of refining the size of the beam path, without requiring smaller tubes whilst also overcoming a problem with the curing process of 3D printers, in which the printed 200 nm tubes may be partially collapsing during the curing process. The first block or segment may have a first array of diamond apertures and the overlaying second block or segment may have a second array of diamond apertures offset from the first array of diamond apertures. As shown in FIG. 13, the superimposition of lumen in blocks may have an aperture size smaller than the apertures of the first array or the second array. When the elongate housing having the superimposition of lumen as similarly illustrated in FIG. 13 with the superimposed lumens being staggered from the central axis is rotated, it may have a spiral appearance as illustrated in FIG. 14 with a full projection as illustrated in FIG. 12.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The claims defining the invention are as follows:

1. An electromagnetic radiation collimator comprising:
   a radiopaque elongated housing having a first end and a second end, wherein the housing houses an array of parallel radiolucent beam paths, wherein each of the beam paths extend from the first end to the second end, wherein each of the beam paths has an entrance aperture at the first end, and an exit aperture at the second end;
   the housing comprising a first layer having a first array of apertures, and a second layer having a second array of apertures; the second layer positioned between the first layer and the second end; such that an aperture from the second layer and an adjacent aperture from the second layer each partially overlaps with an aperture of the first layer;
   the entrance aperture through which source electromagnetic radiation passes into the beam paths, wherein the beam paths emits an electromagnetic radiation beam from the exit aperture when the source electromagnetic radiation beams are in line with the longitudinal axis of the beam path or having a predetermined angle of deviation from the longitudinal axis of the beam path.

2. The electromagnetic radiation collimator according to claim 1, wherein the array of parallel radiolucent beam paths is an array of parallel radiolucent tubes, wherein each of the tubes defines a lumen for providing the beam path, and wherein the radiolucent tubes are embedded in the elongate housing.

3. The electromagnetic radiation collimator according to claim 1, wherein the elongate housing is composed of a series of alternating first and second layers offset relative to each other, wherein the first layer comprises a first set of apertures each having a first shape, and the second layer comprises a second set of apertures each having a second shape, wherein the first shape and the second shape are partially intersecting such that the series of intersected shapes defines a lumen for providing the beam path.

4. The electromagnetic radiation collimator according to claim 1, wherein the first elongated housing has a length longer than a second elongated housing, the width of the entrance aperture of the first elongated housing is smaller than the width of an entrance aperture of the second elongated housing.

5. The electromagnetic radiation collimator according to claim 1, wherein the predetermined angle of deviation from the longitudinal axis of the beam path is less than 10°.

6. The electromagnetic radiation collimator according to claim 5, wherein the predetermined angle of deviation from the longitudinal axis of the tubes is less than 1°.

7. The electromagnetic radiation collimator according to claim 5, wherein the predetermined angle of deviation from the longitudinal axis of the tubes is 0°.

8. The electromagnetic radiation collimator according to claim 1, wherein the material of the elongate housing is one selected from the group of: aluminium, zirconia, titanium, and lead.

9. The electromagnetic radiation collimator according to claim 8, wherein the surface of the device at the end where the X-rays enter is perpendicular to the longitudinal axis of the device.

10. The electromagnetic radiation collimator according to claim 1, wherein the elongate housing comprises at least a groove, wherein the grooves is adapted to engage to a spinning motor for spinning the elongate housing.

11. The electromagnetic radiation collimator according to claim 10, wherein each of the grooves is 3 mm deep, and a width of 5 mm wide.

12. The electromagnetic radiation collimator according to claim 1, wherein the width of each beam paths is 100 microns.

13. The electromagnetic radiation collimator according to claim 1, wherein the electromagnetic radiation is one selected from the group of: X-ray radiation, and UV-C radiation.

14. The electromagnetic radiation collimator according to claim 13, wherein the width of the entrance and exit apertures for use with X-ray radiation are relatively smaller than width of the entrance and exit apertures for use with UV-C radiation.

15. An electromagnetic radiation imaging device adapted for use with two of the electromagnetic radiation collimators of claim 1, the device comprising:
    an electromagnetic radiation source for generating electromagnetic radiation;
    the first electromagnetic radiation collimator positioned between the radiation source and the subject region, such that the subject region is subjected to parallel electromagnetic radiation from the collimator;
    the second electromagnetic radiation collimator positioned between the subject region and an electromagnetic radiation detector, wherein the second electromagnetic radiation collimator is adapted for filtering scattered radiation after propagating through the subject region such that propagated radiation, in line with the longitudinal axis of the beam path of the second collimator allows for the propagated radiation to be detected by an electromagnetic radiation detector.

16. The electromagnetic radiation image device according to claim 15, wherein the electromagnetic radiation source is a rotating anode X-ray source or a UV lamp.

17. The electromagnetic radiation image device according to claim 15 or claim 16, wherein the electromagnetic radiation detector is an X-ray film for X-ray radiation or a UV-C light sensor.

* * * * *